(12) United States Patent
Shalev

(10) Patent No.: US 10,251,460 B2
(45) Date of Patent: Apr. 9, 2019

(54) APPARATUS AND METHOD FOR USING EFFERVESCENT TABLETS FOR COSMETIC CARE

(71) Applicant: POLLOGEN LTD., Tel Aviv (IL)

(72) Inventor: Pinchas Shalev, Herzeliya (IL)

(73) Assignee: POLLOGEN LTD., Tel Aviv (IL)

( * ) Notice: Subject to any disclaimer, the term of this patent is extended or adjusted under 35 U.S.C. 154(b) by 0 days.

(21) Appl. No.: 15/925,504

(22) Filed: Mar. 19, 2018

(65) Prior Publication Data

US 2018/0271253 A1 Sep. 27, 2018

Related U.S. Application Data

(63) Continuation of application No. 15/590,236, filed on May 9, 2017, now Pat. No. 9,949,548, which is a
(Continued)

(51) Int. Cl.
*A61K 8/02* (2006.01)
*A61K 8/19* (2006.01)
(Continued)

(52) U.S. Cl.
CPC ............ *A45D 34/04* (2013.01); *A61K 8/0225* (2013.01); *A61K 8/19* (2013.01); *A61K 8/36* (2013.01); *A61K 8/365* (2013.01); *A61K 8/60* (2013.01); *A61K 8/67* (2013.01); *A61K 8/673* (2013.01); *A61K 8/676* (2013.01); *A61K 8/8176* (2013.01); *A61K 8/86* (2013.01); *A61M 35/003* (2013.01); *A61Q 11/00* (2013.01); *A61Q 19/00* (2013.01); *A61Q 19/10* (2013.01); *A45D 44/00* (2013.01); *A45D 2200/058* (2013.01);
(Continued)

(58) Field of Classification Search
CPC ............ A61K 2800/28; A61K 2800/87; A61K 2800/222; A61K 2800/882; A61K 8/0225; A61K 8/0216; A61K 8/0279; A61K 8/19; A61K 8/673; A61K 8/676; A61K 8/365; A61Q 19/00; A61Q 19/10; A61Q 11/00; A45D 2200/1036; A45D 2200/058; A45D 2200/1054; A45D 2200/1045; A45D 44/00; A45D 34/04; A61M 35/003
See application file for complete search history.

(56) References Cited

U.S. PATENT DOCUMENTS 1,356,544 A * 10/1920 Miller ................. A61J 3/07
424/43
2,312,381 A * 3/1943 Bickenheuser ........... A61J 3/10
424/44
(Continued)

*Primary Examiner* — Joshua Lee
(74) *Attorney, Agent, or Firm* — ISUS Intellectual Property PLL; A. Jason Mirabito

(57) ABSTRACT

An apparatus and method for providing cosmetic treatment to skin comprise one material chemically active in a solid form preferably in a tablet form and a second material which is chemically reactive with the first material so that effervescence is produced during the reaction. The chemically active materials may be activated by a user for providing cosmetic treatment to skin. The activation releases effervescence which urges granules of the reacting materials onto the skin. The size of the granules lowers during the reaction thus providing continuously refining peeling to the skin.

5 Claims, 14 Drawing Sheets

Related U.S. Application Data continuation of application No. 15/279,510, filed on Sep. 29, 2016, now abandoned, which is a continuation of application No. 14/644,325, filed on Mar. 11, 2015, now abandoned, which is a continuation of application No. 13/171,713, filed on Jun. 29, 2011, now abandoned.

(60) Provisional application No. 61/482,302, filed on May 4, 2011.

(51) Int. Cl.

| | | |
|---|---|---|
| *A61K 8/36* | (2006.01) | |
| *A61K 8/60* | (2006.01) | |
| *A61K 8/67* | (2006.01) | |
| *A61K 8/81* | (2006.01) | |
| *A61K 8/86* | (2006.01) | |
| *A45D 34/04* | (2006.01) | |
| *A61K 8/365* | (2006.01) | |
| *A61M 35/00* | (2006.01) | |
| *A61Q 11/00* | (2006.01) | |
| *A61Q 19/00* | (2006.01) | |
| *A61Q 19/10* | (2006.01) | |
| *A45D 44/00* | (2006.01) | |

(52) U.S. Cl.
CPC .......... *A45D 2200/1009* (2013.01); *A45D 2200/1036* (2013.01); *A45D 2200/1054* (2013.01); *A61K 2800/222* (2013.01); *A61K 2800/28* (2013.01); *A61K 2800/87* (2013.01); *A61K 2800/882* (2013.01)

(56) References Cited

U.S. PATENT DOCUMENTS

| | | | | |
|---|---|---|---|---|
| 3,367,545 | A * | 2/1968 | Cook | B05C 17/00516 222/327 |
| 4,487,757 | A * | 12/1984 | Kiozpeoplou | A61K 8/02 424/44 |
| 4,665,901 | A * | 5/1987 | Spector | A61M 35/006 15/227 |
| 4,905,825 | A * | 3/1990 | Brader | A61K 8/365 206/219 |
| 4,993,592 | A * | 2/1991 | Brader | A61K 8/365 206/221 |
| 5,398,850 | A * | 3/1995 | Sancoff | A61M 5/14593 222/386.5 |
| 5,398,851 | A * | 3/1995 | Sancoff | A61M 5/14593 222/386.5 |
| 5,858,001 | A * | 1/1999 | Tsals | A61M 5/14248 604/135 |
| 5,865,799 | A * | 2/1999 | Tanaka | A61M 5/284 604/86 |
| 6,334,727 | B1 * | 1/2002 | Gueret | A45D 33/00 401/190 |
| 6,467,981 | B1 * | 10/2002 | Gueret | A45D 40/00 401/201 |
| 6,506,713 | B1 * | 1/2003 | Slavtcheff | A61K 8/19 424/401 |
| 6,610,312 | B2 * | 8/2003 | Farrell | A47K 7/03 424/401 |
| 6,652,888 | B2 | 11/2003 | Rhoades | |
| 7,416,358 | B2 * | 8/2008 | Legendre | A45D 40/26 401/133 |
| 7,854,938 | B2 * | 12/2010 | Ueda | A61K 8/0212 206/219 |
| 2002/0029478 | A1 * | 3/2002 | Haws | B26B 21/446 30/41.5 |
| 2003/0075200 | A1 * | 4/2003 | Gueret | A45D 34/04 132/320 |
| 2003/0194434 | A1 * | 10/2003 | Watanabe | A61K 8/02 424/466 |
| 2004/2119124 | | 11/2004 | Gupta | |
| 2005/0006401 | A1 * | 1/2005 | Kim | A23L 2/40 222/1 |
| 2006/0128592 | A1 * | 6/2006 | Ross | A61K 8/0208 510/439 |
| 2007/0186951 | A1 * | 8/2007 | Gueret | A45D 34/00 132/320 |
| 2008/0146487 | A1 | 6/2008 | O'Connor et al. | |
| 2008/0241200 | A1 * | 10/2008 | Sojka | A61K 8/0208 424/401 |
| 2008/0317855 | A1 * | 12/2008 | Jolliffe | A61K 9/0065 424/466 |
| 2010/0034889 | A1 * | 2/2010 | Rau | A23L 2/395 424/489 |
| 2010/0179473 | A1 * | 7/2010 | Genosar | A61M 5/14248 604/70 |
| 2010/0240013 | A1 * | 9/2010 | Levine | A61M 35/006 433/215 |
| 2011/0180445 | A1 * | 7/2011 | Hurwitz | A61K 8/0216 206/461 |
| 2011/0201685 | A1 * | 8/2011 | Campbell | A61K 9/0007 514/570 |

\* cited by examiner

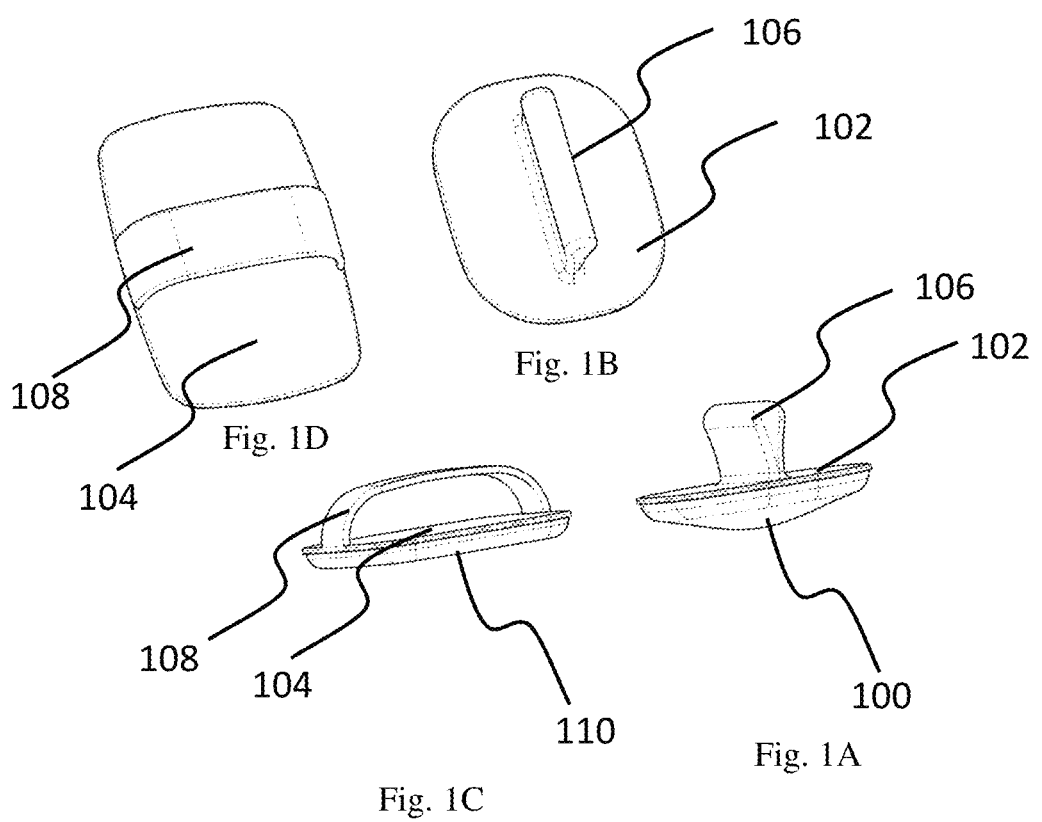

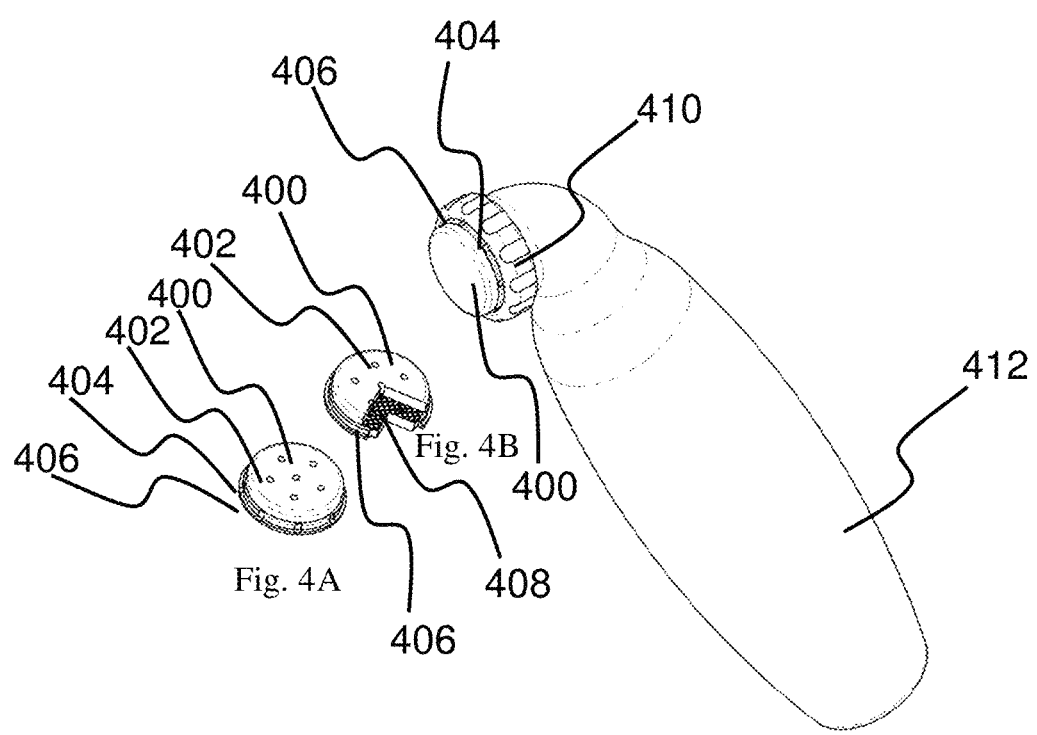

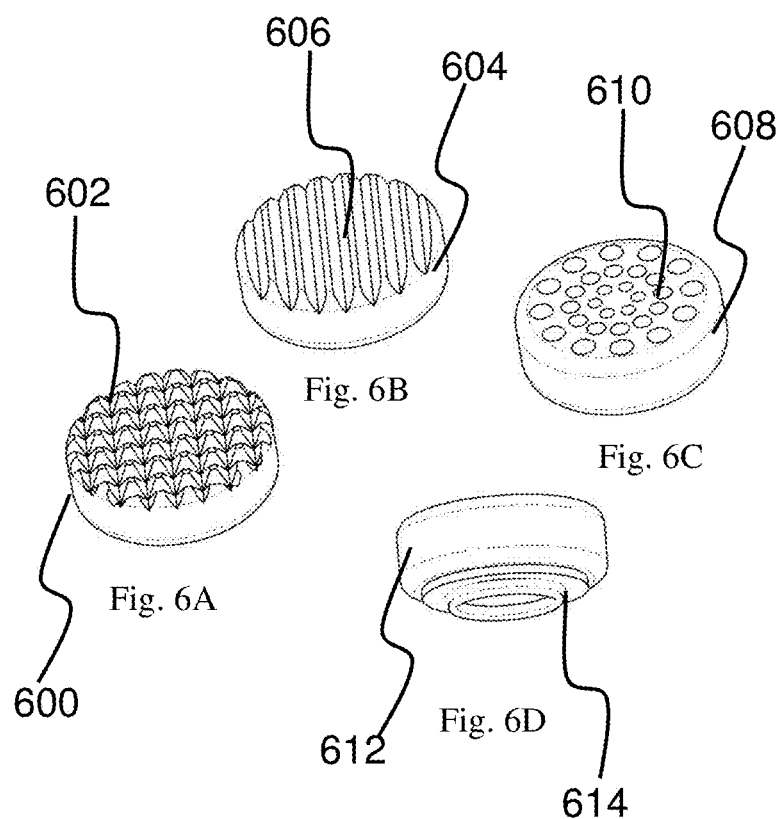

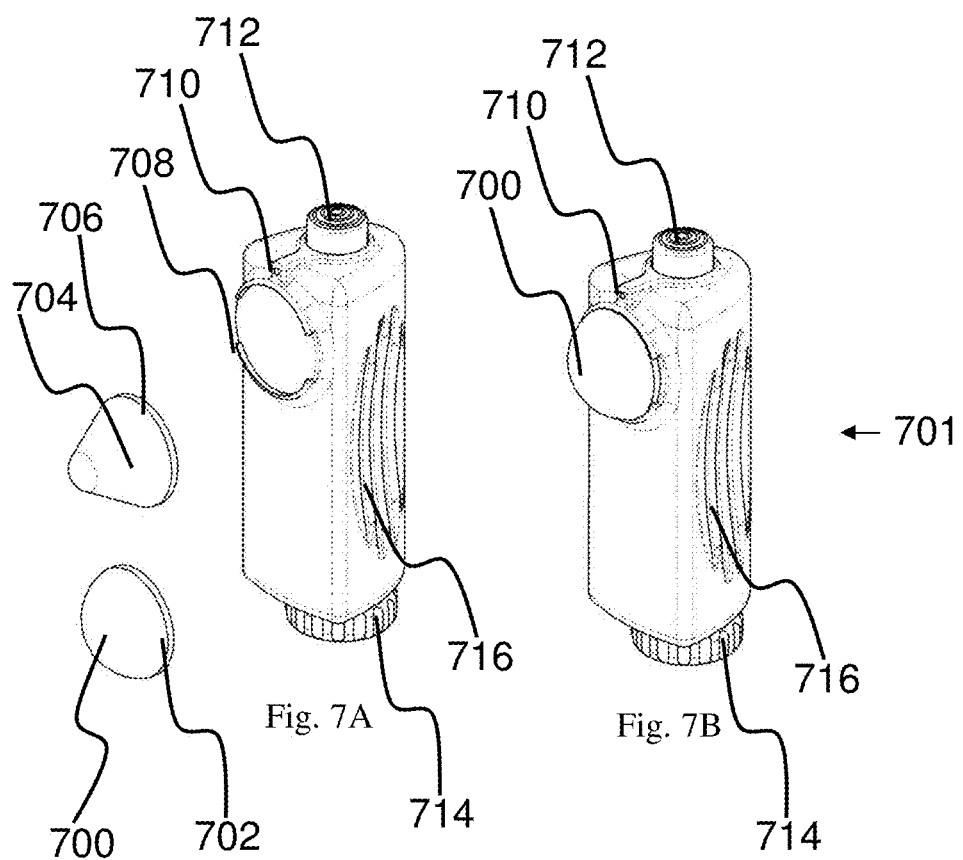

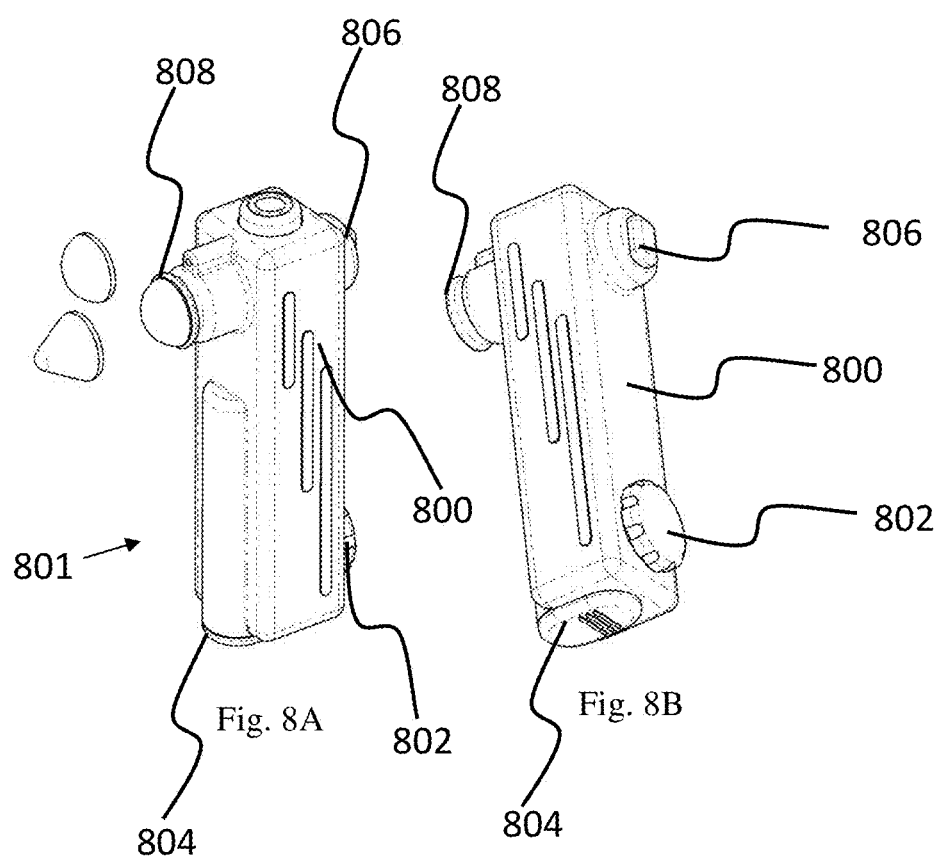

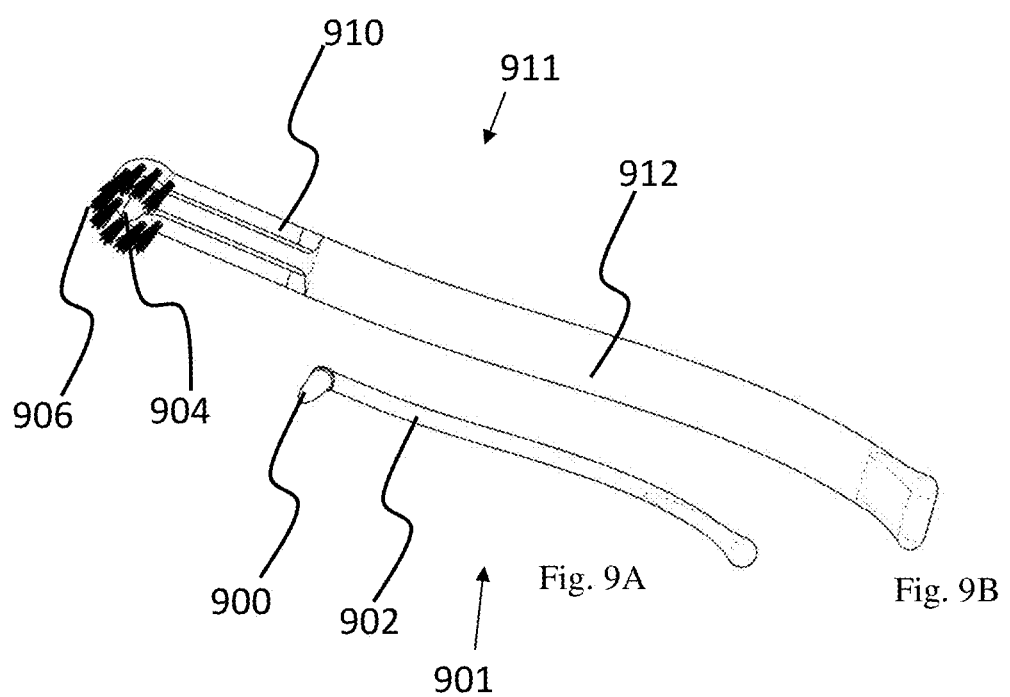

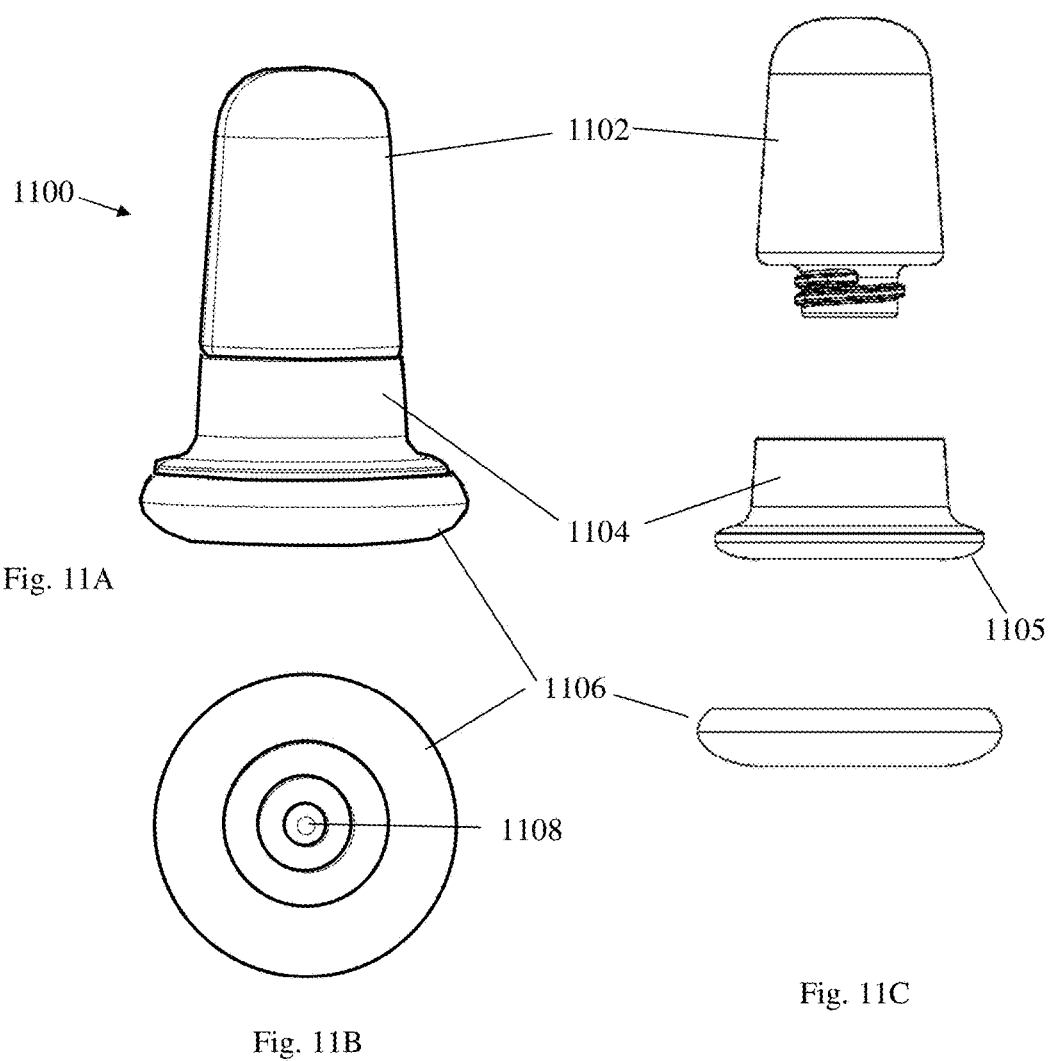

APPARATUS AND METHOD FOR USING EFFERVESCENT TABLETS FOR COSMETIC CARE

CROSS REFERENCE TO RELATED APPLICATIONS

This application is a continuation of U.S. patent application Ser. No. 15/590,236, filed May 9, 2017, which is a continuation of U.S. patent application Ser. No. 15/279,510, filed Sep. 29, 2016, which is a continuation of U.S. patent application Ser. No. 14/644,325, filed on Mar. 11, 2015, which is a continuation of U.S. patent application Ser. No. 13/171,713, filed on Jun. 29, 2011, which claims the benefit of U.S. Provisional Patent Application No. 61/482,302, filed on May 4, 2011, which each incorporated in its entirety herein by reference.

FIELD OF THE INVENTION

The present invention relates to method and apparatus for applying cosmetic treatment to skin and more particular, method for applying cosmetic treatment to skin using effervescent chemical composition and to apparatus for applying such treatment.

BACKGROUND OF THE INVENTION

Facial skin cleaning, brightening or rejuvenating by chemical treatment, laser treatment or by exfoliation using machine driven means are known in the art. Such methods typically require medical supervision and involve some risk of damaging side effects, pain and discomfort during treatment. These methods typically require long recovery time between treatments. Also known in the art are methods for using creams comprising granules (or microcrystals), such as of alumina, which are applied to the outer layers of the skin using mechanical means such as a vibrator. These methods achieve limited level of penetration of the resurfacing microcrystals into the treated skin and suffer of a fix level of skin cells removal as dictated by the size of the microcrystals throughout the treatment.

Method and means for skin treatment that provide high level of penetration of the treating material into the skin, that gradually lowers the level of skin cell removal throughout the treatment to provide improved final level of skin smoothness and that may be safely applied, preferably by the person himself, with no pains or recovery time, are desired. The desired method and means should be inexpensive and easily achievable, virtually anywhere.

BRIEF DESCRIPTION OF THE DRAWINGS

The present invention will be understood and appreciated more fully from the following detailed description taken in conjunction with the appended drawings in which:

FIGS. 1A, 1B, 1C, and 1D show apparatuses for holding a shaped tablet according to embodiments of the present invention;

FIGS. 4A, 4B and 4C and FIGS. 5A and 5B show liquid containers and tablet holders according to embodiments of the present invention;

FIGS. 6A, 6B, 6C and 6D show various shapes of capsule tablets according to embodiments of the present invention;

FIGS. 7A and 7B show various forms of a squirter apparatus comprising capsule shaped tablet according to embodiments of the present invention;

FIGS. 8A and 8B show a squirter similar to the squirter of FIGS. 7A and 7B featuring a rotation and vibration movements applicable to a tablet of the present invention;

FIGS. 9A and 9B show mouth hygiene apparatuses comprising a tablet according to embodiments of the present invention;

FIGS. 11A, 11B and 11C depict skin treatment tool adapted to operate with skin treatment tablet according to embodiments of the present invention, in side view, bottom view and blown view, respectively.

Figure 1:
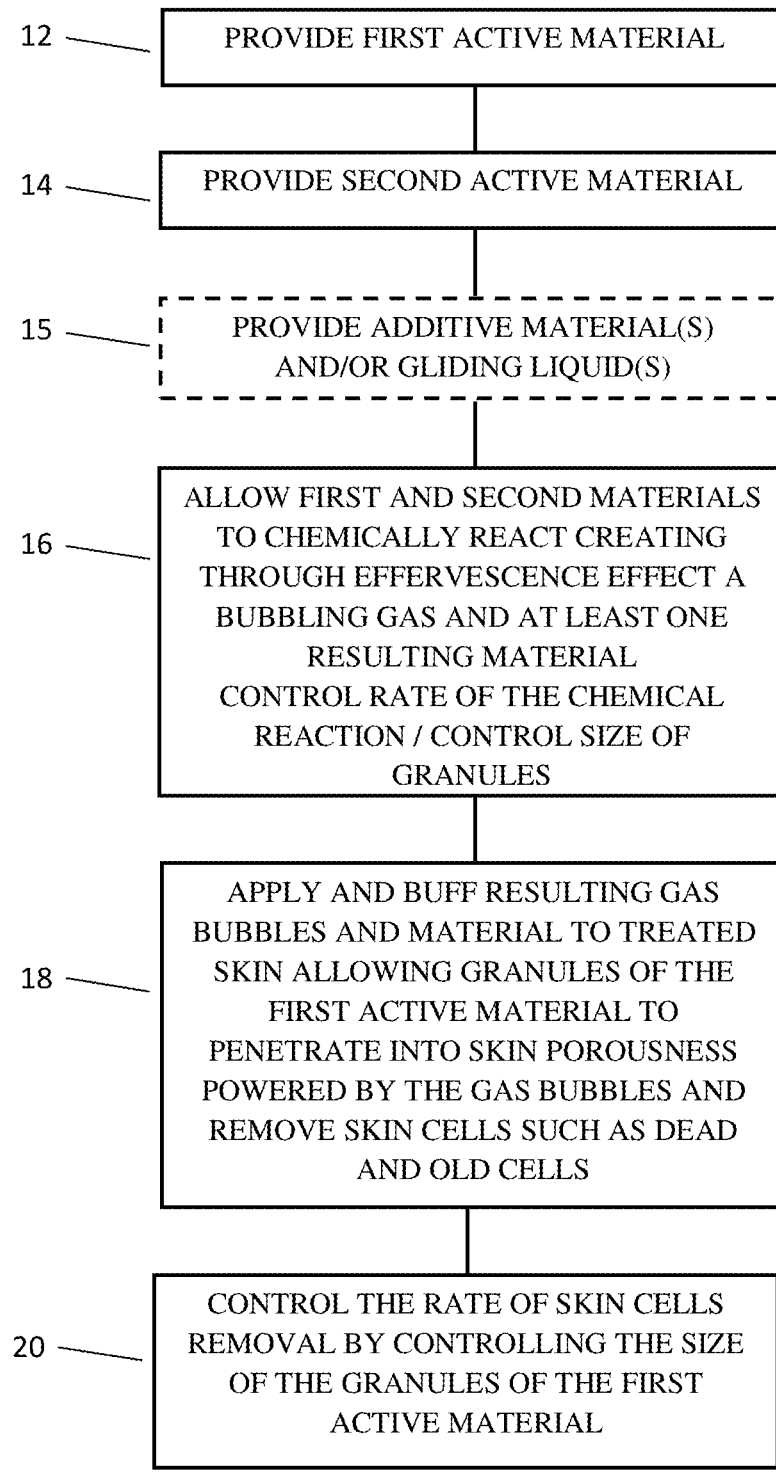
FIG. 1 is a flow diagram illustrating method of applying cosmetic skin treatment, according to embodiments of the present invention.

The following detailed description of the invention refers to the accompanying drawings referred to above. Dimensions of components and features shown in the figures are chosen for convenience or clarity of presentation and are not necessarily shown to scale. Wherever possible, the same reference numbers will be used throughout the drawings and the following description to refer to the same and like parts.

DETAILED DESCRIPTION OF THE INVENTION

Skin treatment in general and cosmetic skin treatment more particularly employ a variety of means and materials aimed to serve a variety of targets, such as removal of the epidermal layer (upper/outer layer) of the skin, lightening the skin color, applying of aromatic or moisturizing materials, applying medical compositions, vitamins or disinfectants, etc. Such treatment means and materials as known in the art are typically expensive and have limited effect due to their limited ability to penetrate into, or through the uppermost outer layer of the epidermal skin layer.

According to embodiments of the present invention the well known phenomena of the effervescence effect of the chemical reaction of certain first and second materials, such as baking soda (sodium bicarbonate) with certain other materials, such as citric acid ($C_6H_8O_{7(aq)}$) may be utilized in cosmetic skin treatment to achieve improved treatment results with respect to the depth of removed epidermis layer, the level of penetration of treating materials into the skin and the final smoothness of the treated skin at the end of the treatment. The first material may be acidic with low value of pH, for example lower than 7 and the second material may be a base with high value of pH, for example higher than 7. As is well known the chemical reaction of baking soda with citric acid is defined by:

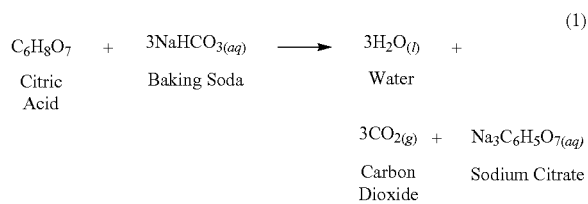

(1)

Similarly, the chemical reaction of tartaric acid with sodium bicarbonate is defined by:

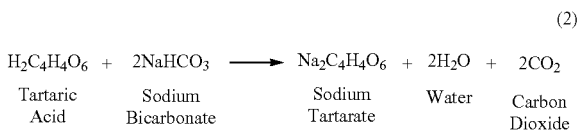

(2)

This phenomenon may be utilized, according to embodiments of the present invention, by using the gas that is released during the reaction (e.g. $CO_2$) to push and force the treating material granules into the treated skin, deeper than is possible without the assistance of the released gas. The treating material may be, according to embodiments of the present invention, merely the granules of the first active material, e.g. baking soda or sodium bicarbonate. In some embodiments the treating material may also contain granules of one or more of materials produced during the chemical reaction. These granules may act on the skin like an emery paper when buffed into the treated skin. The treating reacting material or materials may be buffed into the skin using one or more of the various means presented and described in details below. The phenomenon described above may also be used for skin cosmetic treatment using means other than those described in this application, as long as the reacting at least two materials are applied into the treated skin in a buffing manner. It will be appreciated by a person skilled in the art that other solutions may also be used, which, when reacting, create effervescence effect.

According to one embodiment of the present invention, the reacting materials may be Zeolite and water According to some embodiments, when using Zeolite as a reacting material, pre-charging process may be required, to create a carbonized Zeolite. It will be apparent to a person skilled in the art that carbonized zeolite may release high volumes of carbon dioxide when in contact with water and even with vapor.

It will also be apparent to a person skilled in the art that the first and/or second materials may be provided in any adequate phase, e.g. solid, powder, liquid, gel or gas—as long as their chemical reaction will provide granules and gas. In some embodiments at least one of the first and second active materials may be provided in liquid form (e.g. dissolved in water or the like) or dissolved in gel. The liquid or gel in which one of the active materials is dissolved may be used, according to embodiments of the present invention as a wetting, gliding or oiling material to provide smoother gliding of an apparatus of the present invention with treated skin. According to additional embodiment the carrying liquid and/or gel may be used to provide treating materials to the treated skin. The chemical features of such carrying liquid or gel may be selected as may be desired, e.g. to have no effect on the chemical reaction, to release one or more product materials that has positive effect on the treated skin, as may be required, etc.

According to yet further embodiments of the present invention the continuing decrease in the size of the granules of the reacting first material, e.g. baking soda, zeolite, and the like, due to the chemical reaction, may be utilized for continuous refining of the level of epidermis removal, resulting in refined smoothness of the skin at the end of the treatment. This may last as long as the emery paper effect of the particles is effective for removal and/or smoothing the treated skin. According to embodiments of the present invention the initial size of the granules of the first material may be selected for treatment with a defined level of initial skin removal capacity and the rate of granules size reduction may be controlled to fit the specific treatment needs. It will be appreciated by a person skilled in the art that other solutions may also be used according to embodiments of the present invention which, when reacting, act on the granules of at least one active material to reduce their size during the reaction.

Tablet Compositions and Additives

According to embodiments of the present invention the treating materials may be provided in the form of a tablet that may have defined from, that may contain the required materials for achieving the required treatment goals and that may be applied to the treated skin during the treatment using specially designed apparatuses, as is described in details herein below. The term 'tablet', as used throughout this specification, relates to material or materials that are adapted to participate in a chemical reaction and that are provided in a solid form, having a defined shape, where not all of the materials contained in the tablet necessarily adapted to participate in that chemical reaction. Additionally to treatment effects according to the present invention that were mentioned above, tablets made according to embodiments of the invention may comprise, additionally to the first and second active materials, materials for treating the skin, for lightening its color, for providing odors, for providing vitamins, for casing exothermic effect, etc. The amount of each of the ingredients in a tablet, as well as their order of release, their level of solubility and other respective features may be set so as to fulfill the treatment goals it is designed for, as is explained in details below. US application Publication No. 2008/0146487 (O'Connor et al.), to which reference is made now, describes certain possible uses of tablets with numerous ingredients for providing different phases of user experience when bathing. The described tablets are made for dissolving in the bath water and are made of several layers of the desired materials so that the release of each layer, in its turn, into the bath water, provides different user experience. However, US 2008/0146487 does not disclose or suggest direct application of the tablets on a human's skin for achieving cosmetic treatment effects, nor does it disclose use of the effervescence effect for enhancing the cosmetic treatment effect or reliance on the lessening size of granules of material in the tablet for controlling the cosmetic treatment effect so as to refine the final smoothness of the skin. Moreover, effects of materials included in the tablets described in US 2008/0146487 on the user's skin are limited to the exposure of the skin to their presence next to the user's body, after the tablet is dissolved in the amount of bath water, typically tens of liters or more. For example, use of exothermic ingredients in the tablets disclosed in US 2008/0146487 is expected to have very limited experience effect for a bathing user when this ingredient is dissolved in tens of mild temperature liters of water.

Compositions of Effervescent Tablet

The choice of ingredients for effervescent granules may be deducted both by the requirement of the manufacturing process and the necessity of making a preparation which dissolves in water. The required ingredients are at least one acid or neutral PH material, and at least one base material. The base should release, according to embodiments of the present invention, carbon dioxide upon reaction with the acid or neutral PH materials. Examples of such acids may include tartaric acid and citric acid. Examples of bases include sodium carbonate, potassium bicarbonate, sodium bicarbonate and zeolite. Effervescent granules may usually be prepared from a combination of citric and tartaric acid rather than from a single acid because the use of either acid alone may cause difficulties. When tartaric acid is the sole acid, the resulting granules readily crumble and lack mechanical strength. Citric acid alone may result in a sticky mixture which is difficult to granulate during the manufacturing process. Effervescent salts may include the following ingredients, which may actually produce the effervescence: sodium bicarbonate, citric acid and tartaric acid. When added to water the acids and base may react to liberate carbon dioxide, resulting in effervescence. It should be noted that any acid-base combination which results in the liberation of carbon dioxide could be used in place of this combination as long as the ingredients are suitable for pharmaceutical use.

The reaction between citric acid and sodium bicarbonate and tartaric acid and sodium bicarbonate, which results in liberation of carbon dioxide, has been shown above in formulas (1) and (2). It should be noted that it requires 3 molecules of sodium bicarbonate to neutralize 1 molecule of citric acid and 2 molecule of sodium bicarbonate to neutralize 1 molecule of tartaric acid. The proportion of acids may be varied, as long as the total acidity is maintained and the bicarbonate completely neutralized. Usually it is desired that ratio of citric acid to tartaric acid equals 1:2 so that the desired ratio of the ingredients can be calculated as follows:

(3) Citric acid:Tartaric acid:Sodium bicarbonate=1:2:3.44 (by weight)

The United States Pharmacopeia (USP) 24 includes the following seven monographs, that may be used for tablets according to embodiments of the present invention:
1. Acetaminophen for Effervescent Oral Solution;
2. Aspirin Effervescent Tablets for Oral Solution;
3. Potassium Bicarbonate Effervescent Tablets for Oral Solution;
4. Potassium Bicarbonate and Potassium Chloride for Effervescent Oral Solution;
5. Potassium Bicarbonate and Potassium Chloride Effervescent Tablets for Oral Solution;
6. Potassium and Sodium Bicarbonates and Citric Acid for Oral Solution; and
7. Potassium Chloride, Potassium Bicarbonate, and Potassium.

Lubricants

A perfect lubricant for effervescent products must be nontoxic and water-soluble. Very few traditional lubricants fulfill these requirements. Intrinsic lubricants are added to the powder mixture and consequently included in the formulation. When added in solid form, the lubricant will have to be finely divided. Metal stearates, such as magnesium or calcium stearate that serve as lubricants in conventional tablets, are seldom used as intrinsic lubricants in connection with effervescent tablets due to their insolubility in water. Use of stearates results in an undissolved, foamy, soapy-tasting layer on the surface of the cloudy solution. In addition, normal lubricant concentrations of metal stearates make the tablets hydrophobic, which entails a slow dissolution of the effervescent tablet in the water.

However, very low concentrations of metal stearates can be used to improve the rate of solution of effervescent tablets as the tablet will remain immersed in the water during dissolution and not float to the surface the way a tablet without metal stearate would. A floating tablet presents a smaller surface area to the water than a tablet immersed in the liquid. Sodium stearate and sodium oleate are water-soluble in low concentrations. They have the characteristic soapy taste, which virtually precludes their use in oral effervescent products but can be used for topical applications. A combination of 4% polyethylene glycol (PEG) 6000 and 0.1% sodium stearyl fumarate proved to be a good lubricant for ascorbic acid tablets made by direct compression on a small scale. Sodium chloride, sodium acetate, and D,L-leucine (water-soluble lubricants) also have been suggested for effervescent tablets. The lubricant used in effervescent formulations should combine hydrophobic and hydrophilic properties in order to achieve both good lubrication and a short disintegration time. A medium polar lubricant is the best compromise such as Fumaric acid. Surfactants such as sodium lauryl sulfate and magnesium lauryl sulfate also act as lubricants.

Extrinsic lubrication is provided via mechanisms that apply a lubricating substance, normally paraffin oil, to the tableting tool surface during processing. One method makes use of an oiled felt washer attached to the lower punch below the tip. This washer wipes the die cavity with each tablet ejection. To avoid having tablets stick to the punch faces, materials such as polytetrafluorethylene or polyurethane have been applied to the faces. Another lubrication method sprays a thin layer of lubricant (either liquid or solid lubricant) onto the tool surfaces after one tablet is ejected and before the granulate of the next tablet enters the die cavity. Products containing acetylsalicylic acid do not usually require additional lubrication.

Glidants

Glidants are usually not necessary. Free-flowing granulates, ingredients of appropriate physical form for direct compression, and the large tablet diameters make it possible to exclude the use of glidants.

Antiadherent

The adherence of the granulate or powder mixture to the surfaces of the apparatus used to apply a tablet according to embodiments of the present invention, so-called picking, can be eliminated by using discs, such as those made of polytetrafluorethylene or polyurethane, cemented to the punch surfaces of the apparatus.

Binders

Binders are commonly used when making conventional tablets. The binders are either added in dry form or dissolved in a suitable solvent and then added in connection with a wet-granulation process. Most binders are polymers and increase the plastic deformation of the formulation. The use of binders will normally prevent a rapid dissolution of the effervescent tablet. Effervescent granules may be formulated with binders since their large surface area, when compared with that of the conventional or the effervescent tablet will result in rapid dissolution. At effervescent granulation composed of anhydrous citric acid and $NaHCO_3$ made with dehydrated alcohol as the granulating liquid, citric acid dissolved during the massing function as a binder.

In order to compress ascorbic acid from a combination with $NaHCO_3$, granulation is required. Common water-soluble binders, such as polyvinylpyrrolidone (polyvidone)

or polyvinylpyrrolidone-poly(vinyl acetate)-copolymer, led to a change of color on the part of the ascorbic acid granules. Hydrogenated maltodextrins containing high amounts of maltitol were chosen, according to embodiments of the present invention, from a wide range of dextrins and maltodextrins as possible binders. Maltitol is a suitable binder for ascorbic acid effervescent tablets. Formation of crystal bridges of maltitol is the assumed binding mechanism. PEG 6000 may function both as a binder and as a lubricant.

Disintegrants or Dissolution Aids

Disintegrants, which are used in conventional tablets, are not normally used in effervescent tablets because one of the marketing demands is that a clear solution should be obtained within a few minutes after adding the tablet to a glass of cold water.

Aroma via Flavors or Fragrances

Various dry flavors are available. The flavors used must be water-soluble or water-dispersible. Suitable emulsifier or surfactant may be added for better incorporation of liquid aromatic oils into dry tablet formulation and its better dispersibility on the skin.

Surfactants

This type of excipient is sometimes used to increase the wetting and dissolution rate of drugs and actives. Attention must be paid to the formation of foam.

Antifoaming Agents

To reduce the formation of foam, and consequently the tendency of additives to the tablet to stick surfaces nest to the water border line, an antifoaming agent, such as polydimethyl-siloxane, can be used. However, antifoaming agents do not normally form constituents of effervescent products.

Stability

The greatest problem with effervescent products is the loss of reactivity with time if exposed prematurely to moisture (i.e., the stability of the effervescent system). In addition, the stability of tablet additives and some excipients, such as flavors, also must be considered. Effervescent compositions may be markedly stabilized if the $NaHCO_3$ is partly converted to the corresponding carbonate. Usually, the desired degree of stability is attained if approximately 2-10% of the weight of the bicarbonate is converted to the carbonate.

Potential Cosmetic Actives

Vitamins

Water soluble vitamins which can be incorporated in a powder form are preferred: Vitamin C (Ascorbic acid—can serve also as acid for effervescent reaction), group of Vitamins B (B1 (thiamin), B2 (riboflavin), B3 (Niacin), B6 (pyridoxine), Pro-vitamin B5 (Panthenol), B9 (Folic Acid), B12 (cobalamin). But to some extent, fat soluble vitamins such as A, E, D, F, K and their derivates and co-enzymes can be added for a spread on and rubbing/massage stage of topical application. Vitamins can serve as moisturizing, anti-oxidant, wrinkle reduction, skin whitening and anti-acne activity.

Plants Extracts

Plant extracts in powder form can be used in both water soluble and water non-soluble forms. Water non-soluble powder plant extracts can serve as a natural mechanical peeling and toxins/dirt absorbing agent. Plant extracts can serve as moisturizing, anti-oxidant, wrinkle reduction, skin whitening, slimming and anti-acne activity, for example caffeine. Plant extracts and oils can serve also as aromatic additives.

Alpha and Beta Hydroxy Acids

Malic, maleic, lactic, salicylic, fruit acids, glycolic acid, hydroxyoctanoic acid, azelaic acid and mixtures of these as well as their salts may serve as chemical peeling for wrinkle reduction, skin whitening and anti-acne activity.

Amino Acids and Proteins

These actives are mostly water soluble powders, and may serve as moisturizing and film forming/emollients agents during and after application of the cosmetic skin treatment according to embodiments of the present invention. Suitable amino acids include, e.g., L-tyrosine, isoleucine, ornithine, glutamine, phenylalanine, leucine, lysine, methionine, threonine, taurine, tryptophan, valine, alanine, glycine, arginine, histidine, cysteine, asparagine, proline and serine, and mixtures thereof.

Polyssacharides

Polysaccharides that may be useful according to embodiments of this invention are dry solid anhydrous substances such as sorbitol, sugars, (such as trehalose) starches, modified starches (e.g. aluminum octenyl succinate) and mixtures thereof. These actives are water soluble powders, can serve as moisturizing and film forming/emollients agents during and after application. Their film forming activity has usually a soothing effect. Alginic acid, guar gum and algae extracts are typical examples. These materials may also serve as dirt absorbing and water swelling medium during and after application. Starches are also suitable emollients. Typical of this class is tapioca and arabinogalactan. Furthermore, polyssacharides and their derivates can serve as tablet formulation binders: starches, natural gums, cellulose gums, microcrystalline cellulose, methylcellulose, cellulose ethers, sodium carboxymethylcellulose, ethylcellulose, gelatin, dextrose, lactose, sucrose, sorbitol, mannitol, polyethylene glycol, polyvinylpyrrolidone, pectins, alginates, polyacrylamides, polyvinyloxoazolidone, polyvinylalcohols and mixtures thereof.

Gliding Agent

Gliding agent, such as PEG-14M (usable in shaving gels), can ease the gliding of tablet on the skin during the application. It also can serve as binder during tablet production.

Minerals

Examples of minerals which may be used as additives to tablets for skin treatment according to embodiments of the present invention include calcium, iron, zinc, selenium, copper, iodine, magnesium, phosphorus, chromium and mixtures thereof. The base which is capable of generating carbon dioxide is also considered as mineral. Examples of suitable carbonate bases include sodium bicarbonate, sodium carbonate, sodium sesquicarbonate, potassium carbonate, potassium bicarbonate, calcium carbonate, magnesium carbonate, magnesium oxide, sodium glycine carbonate, L-lysine carbonate, arginine carbonate, zinc carbonate, zinc oxide, zeolite and mixtures thereof. Some natural minerals such as sodium or magnesium, magnesium silicate and bentonites can serve also as swelling agents. Some minerals such as magnesium oxide or zeolites can also serve for exothermic effect during water addition.

Disinfectants

Antibacterials and fungicidals may be included as skin benefit agents. Representative of these categories are triclosan, tricloban, hexetidene, chlorhexadene, gluconates, zinc salts (e.g. zinc citrate and zinc phenolsulfonate) and combinations thereof. Benzoyl peroxide is known as very effective treatment for acne and may be added to tablet for skin treatment according to embodiments of the present invention.

Pain Relief and Anti-Inflammatory Agents

Menthol, camphor, methyl salicylate, clove oil, allantoin, benzyl alcohol may be used as pain relief and/or inflammatory agents for use as ingredients of a tablet for skin treatment according to embodiments of the present invention.

Surfactants

Surfactants such as polysorbate 80 and sodium lauryl sulfate may serve for cleansing of the skin or as surfactant aid during tablet formulation when added to tablets for skin treatment.

Natural or Synthetic Oils and Waxes

Emollients may be in the form of natural or synthetic esters/waxes, silicone oils/waxes, hydrocarbons, starches, fatty acids and mixtures thereof, including bees wax, silicon waxes, bee pollen, bran, wheat germ, kelp, cod liver oil, ginseng, and fish oils, glucosamine, chondroitin, methylsulfonylmethane, and mixtures thereof.

Peptides

A long list of additives may be included in skin treatment tablets for anti-aging activity, according to embodiments of the present invention.

Skin Lighteners

Additives typical of this category that may be added to skin treatment tablets are niacinamide, kojic acid, arbutin, vanillin, ferulic acid and esters thereof, resorcinol, hydroquinone, placental extract and combinations thereof.

Typical Formulation Example

One effervescent tablet made with weights 1.5 grams (1500 mg), formula for 1 piece of Vitamin C effervescent tablets:

Vitamin C 500 mg
Pyridoxine 20 mg
PVP 3% 45 mg
Sucrose 15% 225 mg
Citric Acid Monohydrate 208 mg
Tartaric Acid 222.9 mg
PEG 8000 30 mg Calculations Exemplary calculations for 1500 mg tablet for cosmetic skin treatment according to embodiments of the present invention:

Weight of effervescent tablet=1500 mg
Inner Phase weight (consist of active ingredient, acid, base, binder and filler) (98%)=98/100×1500 mg=1470 mg
Outer Phase (consists of glidant) (2%)=2/100×1500 mg=30 mg
Acid and Base weight=Inner phase−(active ingredient+binder+filler)=1470 mg−(520+45+225) mg=680 mg
Citric acid monohydrate:
  Molecular weight=210.13
  Equivalent number=3
  Equivalent weight=210.13/3=70.04
Tartaric Acid:
  Molecular weight=150.09
  Equivalent number=2
  Equivalent weight=150.09/2=75.05
Sodium Bicarbonate:
  Molecular weight=84.01
  Equivalent number=1
  Equivalent weight=84.01/1=84.01
70.04 mol Equivalent+75.05 mol Equivalent+84.01 mol Equivalent=680 mg
229.1 mol Equivalent=680 mg
mol Equivalent=2.97
Citric acid monohydrate=70.04×2.97=208 mg
Tartaric Acid=75.05×2.97=222.9 mg
Sodium Bicarbonate=84.01×2.97=249.5 mg Consideration of Materials in the Formula and Method of Manufacture Selection A preferable binder for use in the preparation of skin treatment tablets according to embodiments of the present invention is PVP because PVP is a water soluble binder and a selected concentration of 3% of PVP for use as a hinder may be selected because in pharmaceutical formulations and technology a typical range is 0.5 to 5%. As filler sucrose may be used, because filler used in the effervescent tablet is sugar. The concentrations of the selected filler may be, e.g. 15%. The acid that may be used is a combination of citric acid monohydrate and tartaric acid which is adapted to formulate tablets with strong effervescent effect. When using citric acid monohydrate only, the produced granules may be sticky and soft, so it can not be compressed, whereas when used in single-tartaric acid the produced effervescent tablets may be hard and crack able. Sodium bicarbonate may be used as base. PEG 8000 may be used as lubricant.

Applying Cosmetic Skin Treatment

Reference is made now to FIG. 1, which is a flow diagram illustrating method of applying cosmetic skin treatment, according to embodiments of the present invention. A first active material and a second active material (blocks 12 and 14) are provided. These materials may be included in a tablet and may be activated in the presence of a liquid, such as water, gel or other kinds of liquid. Optionally gliding liquid, such as water or gel and/or additives of various kinds and for various purposes may also be provided (block 15), as discussed in details above. The first and second active materials are allowed to chemically react and to liberate gas (such as carbon dioxide) through effervescent effect (block 16). According to some embodiments only one active material is required which may be activated when exposed to an activating material such as water. Additionally, during the chemical reaction size of granules of at least the first active material may be lessened due to the chemical reaction. The rate of the chemical reaction may be controlled, for example by controlling the rate of supply of the activating material, by controlling the temperature of the reaction or its pressure, etc. As a result of the effervescent effect granules of at least the first active material may penetrate into the treated skin deeper than in known cosmetic treatments and therefore may remove undesired skin cells from deeper skin layers. The effervescent effect may also assist in providing the additives of the treatment tablet deeper into the skin layers. In case when exothermic additives are used the exothermic effect may amplify the penetration effect of the bubbling gas even more.

The skin treatment tablet may be applied onto the treated skin using one of the various tablet holders/holding means described in details below by providing buffing movements over the skin on the treated area (block 18) resulting removal of undesired layers of skin.

The rate of the chemical reaction may be controlled to control one or more of the rate of lessening of the size of granules of the first active material and the amount of gas produced during the chemical reaction (block 20).

Means for Applying Cosmetic Treatment Tablets

Illustrative embodiments of means for applying cosmetic treatment tablets according to embodiment of the present invention are described below. In the interest of clarity, not all features/components of an actual implementation are necessarily described.

FIGS. 1A, 1B, 1C, and 1D show apparatuses for holding a shaped tablet according to embodiments of the present invention comprising a tablet 100; and structures 102 or 104. Tablet 100 can be shaped into various shapes. The shaped tablet can be fitted with various structures and devices. In this preferred embodiment, solid 100 is shaped into a curved surface and may be fitted within structure 102, 104. Structures 102, 104 include handle 106, 108 respectively. Handle 106, 108 allow the user to scrub solid 100 against user's body. By wetting the area to be scrubbed and scrubbing the area with tablet 100, tablet 110 dissolves while cleaning the area. The scrubbing further generates cleaning foam.

Figures 2A, 2B:
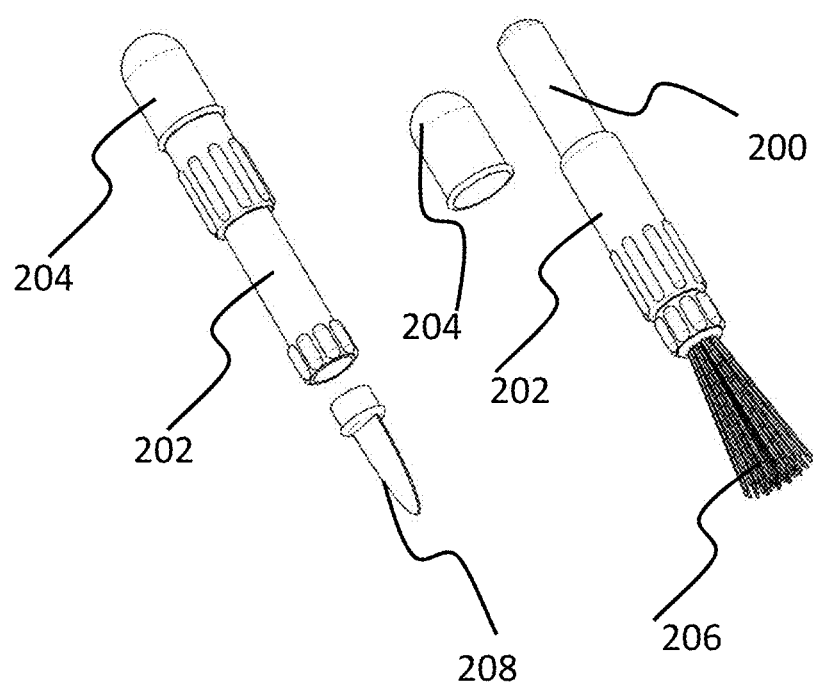
FIGS. 2A and 2B show apparatuses for holding a shaped tablet according to embodiments of the present invention.

FIGS. 2A and 2B show apparatuses for holding a shaped tablet according to embodiments of the present invention. Apparatus 202 may be shaped as a lipstick container, comprising solid 200 shaped as stick; and a brush 206 or scrapper 208. Container 202 can rotate to expose/hide solid 200, similar to operation of a lipstick container. Cap 204 may be used to cover the remaining of the exposed solid 200.

Attachments 206, 208 may be used to scrub the user's skin while generating foam with the remains of the dissolved solid, or to scrub the skin with the foamed solid. The attachments may be removed and replaced as needed.

Figures 3A, 3B:
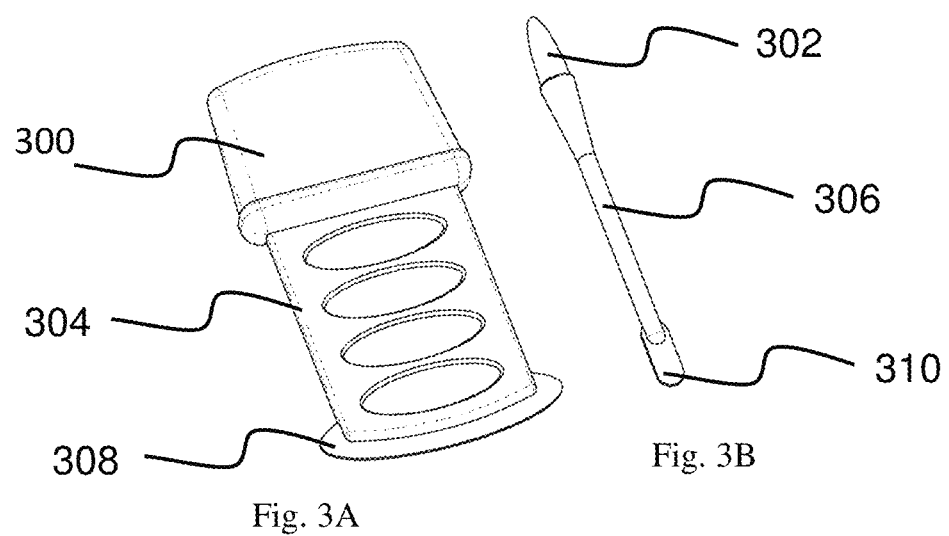
FIGS. 3A and 3B depict applicators for holding a shaped tablet according to embodiments of the present invention.
Figures 5A, 5B:
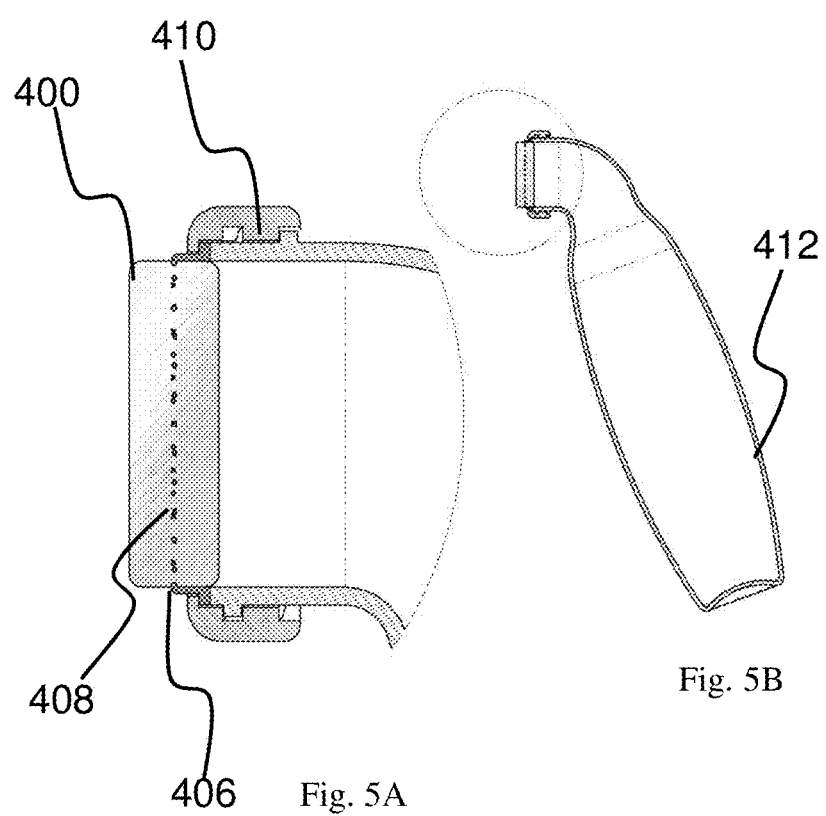

FIGS. 3A and 3B depict applicators for holding a shaped tablet according to embodiments of the present invention. Applicators 304; 306 are shaped as wide and narrow applicators, respectively. Applicators 304, 306 comprise solids/tablets 300, 302 and scrappers 308, 310, respectively.

FIGS. 4A, 4B and 4C and FIGS. 5A and 5B show liquid containers and tablet holders according to embodiments of the present invention. Tablet 400 may comprise channels 402 allowing liquids to pass through while dissolving the tablet. Tablet 400 may further comprise mounting base 408 shaped as a web. Mounting base 408 may be meshed within solid 400, thus allowing affixing a dissolved tablet. Mounting base 408 may be mounted within connector 406. Connector 406 may further comprise holes 404. Holes 404 may allow liquids, for example from container 412, to pass through while wetting the surface in contact with tablet 400. Sealer 410 may fit connector 406 over the opening of squeezable container 412. Squeezing squeezable container 412 may extract contained liquids throughout holes 404 and/or channels 402 while dissolving tablet 400. The inner surface of tablet 400 which faces the inner part of the squeezable container opening, may dissolve and foam while creating pressure within container 412. The inner foam is also pressurized extract with the squeezed liquids.

FIGS. 6A, 6B, 6C and 6D show various shapes of capsule tablets according to embodiments of the present invention. Tablet 600 may comprise projections 602; Tablet 604 may comprise stripes 606 and tablet 608 may comprise holes 610. Tablet 612 may comprise meshed snap-on locator 614.

FIGS. 7A and 7B show various forms of squirter 701 comprising capsule shaped tablet according to embodiments of the present invention. Solid 700, 704 may comprise adjustment ring 702, 706 respectively. Adjustment ring 702, 706 may fit within niche 708. Pressing button 712 may squirt contained liquids through nozzle 710. Squirting contained liquids from within container 716, while rubbing affixed tablet 700, 704 may scrub the skin while dissolving the solid over the rubbed skin. Cap 714 can be removed in order to fill, refill or empty container 716.

FIGS. 8A and 8B show squirter 801 similar to squirter 701 of FIGS. 7A and 7B featuring a rotation and vibration movements applicable to the solid/tablet of the present invention. A preferred embodiment of Squirter 801, as based on squirter 701, may further comprise batteries cap 804, rotation and/or vibration activation button 806 and rotation and/or vibration movement source 808 fitted with the solid. Activating the rotation and/or vibration source during treatment may further scrub the solid against the skin. The activation button further controls the squirting through the nozzle. Cap 802 can be removed in order to fill or empty container 800.

FIGS. 9A and 9B show mouth hygiene apparatuses 901, 911 comprising a solid/tablet according to embodiments of the present invention. Apparatus 901 comprising handle 902 adapted to hold solid 900 at its end, wherein solid 900 may be shaped to enable scrubbing inside the mouth cavity. Solid 900 may fit the size of tooth, between tooth, and tongue. Apparatus 911 may comprise handle 912 comprising bristles 906 fitted over flexible arm 910. Flexible arm 910 allows bristles 906 to withdraw during brushing thus keeping the remains of the dissolved solid 904 in contact with the brushed surface.

Figures 10A, 10B, 10C:
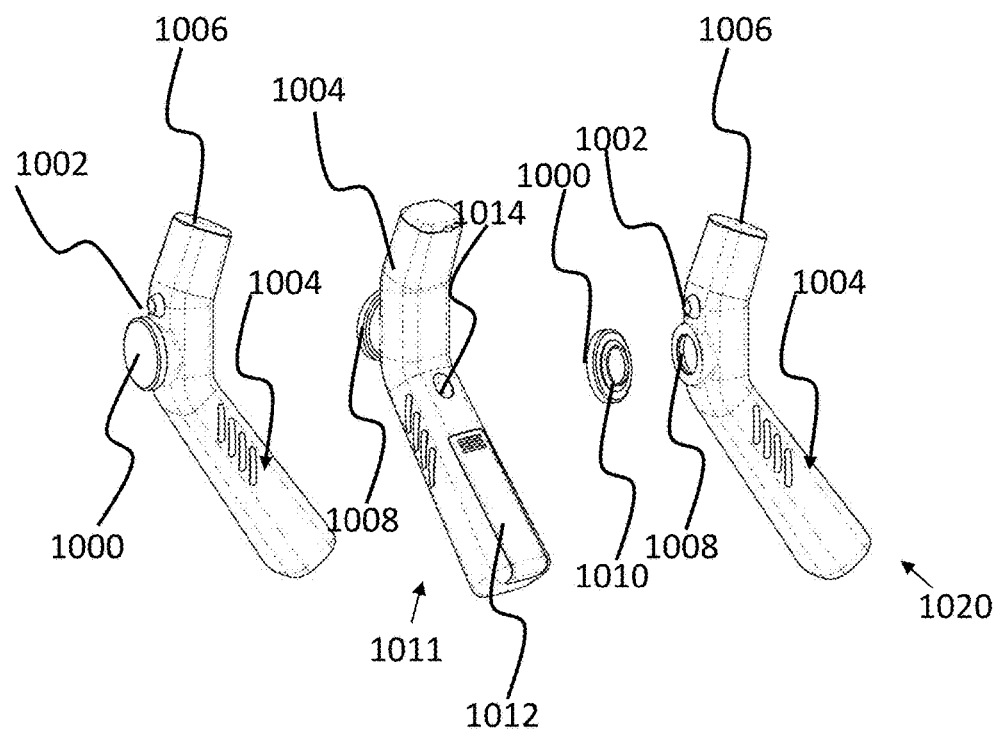
FIGS. 10A, 10B and 10C show handheld evaporative humidifier apparatuses comprising each a tablet according to embodiments of the present invention.

FIGS. 10A, 10B and 10C show handheld evaporative humidifier apparatuses 1004, 1011 and 1004, respectively, comprising a solid/tablet according to embodiments of the present invention. Handheld evaporative humidifier 1004 may generate fogged liquids. The fogged liquids may wet the area in front of nozzle 1002 thus foaming scrubbed solid 1000. Controller 1014 may control the evaporator, for example by inducing an electrical field with changing filed strength. Handheld evaporative humidifier 1004 may comprise lid 1006 for filling/refilling contained liquids, and power source chamber 1012 for placing/replacing power source unit, such as batteries/chargeable batteries. Solid 1000 may comprise snap on cap 1010 which may be adapted to fit onto connector 1008.

Reference is made to FIGS. 11A, 11B and 11C, which depict skin treatment tool 1100 adapted to operate with skin treatment tablet 1106, according to embodiments of the present invention, in side view, bottom view and blown view, respectively. Apparatus 1100 may comprise gel container 1102 which is formed to contain gel and to be used also as a handle. Gel container 1102 may be connected to mediator element 1104 at a first end of it. Mediator 1104 may comprise a gel passage allowing gel to flow from gel container 1102 towards tablet 1106 connectable to the other end mediator 1104. Tablet 1106 may be formed to fit onto the other end of mediator element 1104 and may be connected to it by one of various possible means, such as snap-to, adhesive, and others. Tablet 1108 may be formed with hole 1108 in it. Hole 1108 may fit the gel passage (not shown) leading gel from gel container 1102 so as to allow gel to flow through it and wet the outer surface of tablet 1106. The outer circumference 1105 of mediator 1104 may be formed with rounded and soft edge on the side facing the treated skin to provide soft and smooth touch with the skin when approaching the end of the tablet during treatment. Outer circumference 1105 may be formed to protrude outwardly from the diameter of gel container 1102, to prevent undesired touch of long nails with the treated skin.

Figure 12:
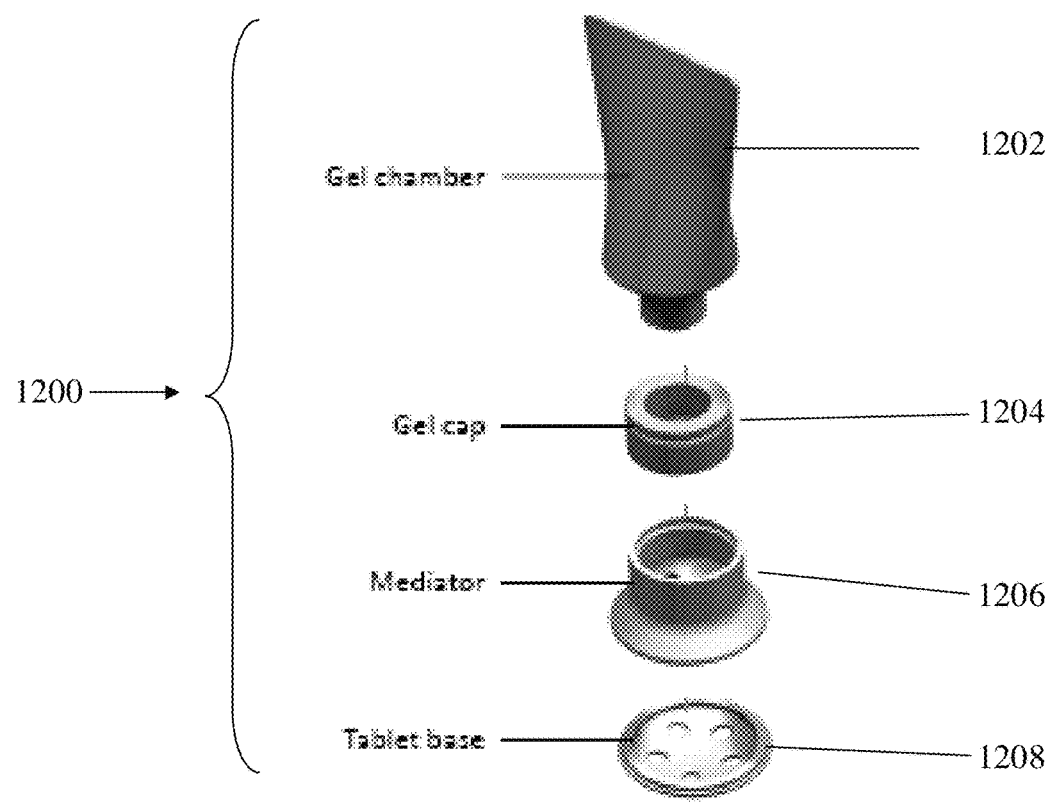
FIGS. 12, 12A and 12B depict a blow-up view of skin treatment tool 1200, a partial sectional view of treatment tool 1202 and a top view of mediator 1206, respectively, according to embodiments of the present invention.
Figures 12A, 12B:
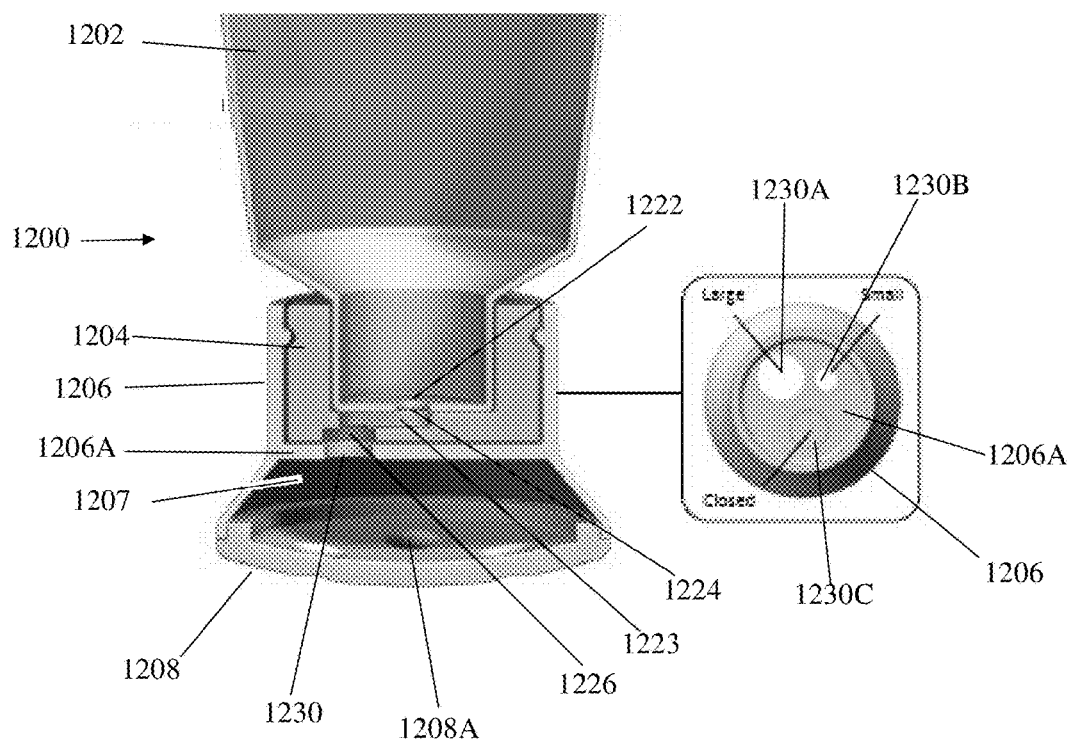

Reference is made now to FIGS. 12, 12A and 12B which are a blow-up view of skin treatment tool 1200, a partial sectional view of treatment tool 1202 and a top view of mediator 1206, respectively, according to embodiments of the present invention. Skin treatment tool 1200 may comprise gel container 1202 comprising gel passage 1222 at one end. Tool 1200 may further comprise gel cap/adaptor 1204 adapted to receive gel container or compartment 1202, for example by snap-on or thread connecting means. Gel cap 1204 comprises also gel passage 1223 adapted to receive flow of gel from gel container 1202 through input passage 1224 and is made so that its output passage 1226 is located off-center of cap 1204, so that when mediator 1206 is rotated with respect to cap 1204 one of several holes 1230 made in mid-partition 1206A, each having different diameter, may be placed, one at a time, against output end passage 1226 of gel, thus providing control means of the rate of flow of gel towards mediator 1206. Mediator 1206 may further comprise tablet compartment 1207 formed to comprise treatment tablets according to embodiments of the present invention. Tablet compartment 1207 may be capped by tablet cap 1208 adapted to connect onto mediator 1206 so as to close tablet compartment 1207 and contain a tablet in there. Tablet cap 1208 may comprise gel outlet hole 1208A, made to allow flow of gel out side of tool 1200. As shown in FIG. 12B mediator 1206 may have made in its mid-partition 1206A several holes (or gel passages) 1230A, 1230B, etc., each having different diameter to provide different gel flow capacity. Mid-partition 1206A may also comprise blocked passage location 1230C to allow inactive mode of tool 1200. It would be apparent to one skilled in the art that mid-partition 1206A may comprise more than two holes with different diameters. It would also be apparent to a person skilled in the art that other means of controlling the rate of flow of gel may be employed without departing from the scope of embodiments of the present invention.

It should be understood that the above description is merely exemplary and that there are various embodiments of the present invention that may be devised, and that the features described in the above-described embodiments, and those not described herein, may be used separately or in any suitable combination, and the invention can be devised in accordance with embodiments not necessarily described above.

The invention claimed is:

1. A tablet for cosmetically treating skin tissue comprising:
    the tablet comprising at least a first active material and at least a second active material, one of the active materials including a base material and the other of the active materials including an acid material, said first and said second active materials being in solid form, the tablet having two opposed faces, an outer, exposed face and an inner-facing face;
    the tablet further comprising a mounting base, the mounting base being formed about the periphery of the tablet;
    the mounting base further comprising a connector for attaching the tablet to a handpiece;
    the base material of the tablet substantially comprising sodium bicarbonate and the acid material substantially comprising citric acid;
    the proportion of the base material to the acid material being 3:1;
    wherein, upon activation by an activating material, the activating material being in a non-solid form, carbon dioxide is produced by the reaction of the acid material and the base material;
    further comprising a handpiece, the tablet being connectable at an opening of the handpiece at the inner-facing face ad around the periphery of the outer face of the tablet;
    the handpiece enclosing a volume to contain the activating material;
    the handpiece opening providing access to the volume;
    wherein the activating material contacts the outer, exposed face of the tablet and produces carbon dioxide;
    wherein the carbon dioxide creates an effervescent effect within the tablet;
    wherein at least some of the effervescent effect takes place on the outer, exposed face of said tablet; and,
    wherein the first active material contains granules for engaging and treating the skin tissue.

2. The tablet of claim 1, wherein the handpiece is squeezable and wherein the act of squeezing the handpiece causes the activating material to leave the handpiece and pass through one or more through apertures formed in the tablet.

3. A tablet for cosmetically treating skin tissue comprising:
    the tablet comprising at least a first active material and at least a second active material, one of the active materials including a base material and the other of the active materials including an acid material, said first and said second active materials being in solid form, the tablet having two opposed faces, an outer, exposed face and an inner-facing face;
    the tablet further comprising a mounting base, the mounting base being formed about the periphery of the tablet;
    the mounting base further comprising a connector for attaching the tablet to a handpiece;
    the base material of the tablet substantially comprising sodium bicarbonate and the acid material substantially comprising citric acid;
    the proportion of the base material to the acid material being 3:1;
    wherein, upon activation by an activating material, the activating material being in a non-solid form, carbon dioxide is produced by the reaction of the acid material and the base material;
    further comprising the one or more of the acid material or the base material are in the form of granules, and wherein, upon activation by the activating material, at least some of the granules are released to and pushed into contact with the skin tissue by the carbon dioxide to provide buffing of the skin tissue.

4. A method comprising:
    providing the tablet for cosmetically treating the skin tissue of claim 3;
    passing activating material onto the tablet to cause the tablet to effervesce on the exposed face of the tablet;
    engaging and rubbing the exposed face of the tablet against the skin tissue, including engaging the skin tissue, thereby cosmetically treating the skin tissue.

5. A tablet for cosmetically treating skin tissue comprising:
    the tablet comprising at least a first active material and at least a second active material, one of the active materials including a base material and the other of the active materials including an acid material, said first and said second active materials being in solid form, the tablet having two opposed faces, an outer, exposed face and an inner-facing face;
    the tablet further comprising a mounting base, the mounting base being formed about the periphery of the tablet;
    the mounting base further comprising a connector for attaching the tablet to a handpiece;
    the base material of the tablet substantially comprising sodium bicarbonate and the acid material substantially comprising citric acid;
    wherein, upon activation by an activating material, the activating material being in a non-solid form, carbon dioxide is produced by the reaction of the acid material and the base material;
    further comprising the one or more of the acid material or the base material are in the form of granules, and wherein, upon activation by the activating material, at least some of the granules are released to and pushed into contact with the skin tissue by the carbon dioxide to provide buffing of the skin tissue.

\* \* \* \* \*